(12) United States Patent
Jensen et al.

(10) Patent No.: US 7,165,466 B2
(45) Date of Patent: Jan. 23, 2007

(54) APPARATUS AND METHOD FOR IN SITU MEASURING OF EVAPORATION FROM A SURFACE

(75) Inventors: Ole Mejlhede Jensen, Aalborg (DK); Per Freiesleben Hansen, deceased, late of Røskilde (DK); by Kirsten Højst Hansen, legal representative, Solrød Strand (DK)

(73) Assignee: Curing Meter A/S, København K (DK)

( * ) Notice: Subject to any disclaimer, the term of this patent is extended or adjusted under 35 U.S.C. 154(b) by 182 days.

(21) Appl. No.: 10/483,675

(22) PCT Filed: Jul. 11, 2002

(86) PCT No.: PCT/DK02/00487

§ 371 (c)(1),
(2), (4) Date: Sep. 1, 2004

(87) PCT Pub. No.: WO03/006986

PCT Pub. Date: Jan. 23, 2003

(65) Prior Publication Data

US 2005/0041721 A1    Feb. 24, 2005

(30) Foreign Application Priority Data

Jul. 13, 2001  (DK)  ............ PA 2001 01106
Oct. 24, 2001  (DK)  ............ PA 2001 01559

(51) Int. Cl.
*G01N 25/02* (2006.01)
*G01N 33/00* (2006.01)
(52) U.S. Cl. .......................... 73/866; 374/53
(58) Field of Classification Search .......... 73/866, 73/73; 374/53
See application file for complete search history.

(56) References Cited

U.S. PATENT DOCUMENTS

| 1,332,659 | A | * | 3/1920 | Bates | ............ 239/44 |
| 4,324,132 | A | * | 4/1982 | Williams | ............ 73/61.77 |
| 4,409,834 | A | * | 10/1983 | Kethley | ............ 73/61.77 |
| 4,418,576 | A | * | 12/1983 | White | ............ 73/61.77 |
| 4,480,929 | A | | 11/1984 | Hansen | |
| 4,762,423 | A | * | 8/1988 | Basta | ............ 374/31 |
| 5,890,491 | A | * | 4/1999 | Rimkus | ............ 128/206.11 |

* cited by examiner

*Primary Examiner*—Hezron Williams
*Assistant Examiner*—Ryan Christensen
(74) *Attorney, Agent, or Firm*—James Creighton Wray

(57) ABSTRACT

The present invention concerns a method for in situ measuring of evaporation from a surface and an apparatus for measuring the evaporation from a surface. The apparatus comprises an evaporation surface made of a porous, hydrophilic material, which surface is connected to a reservoir. The method describes how to use the apparatus according to the invention.

11 Claims, 5 Drawing Sheets

Nomogram: ACI 305R-91
Hot Weather Concreting

APPARATUS AND METHOD FOR IN SITU MEASURING OF EVAPORATION FROM A SURFACE

BACKGROUND

This application claims the benefit of Danish Application No. PA 2001 01106 filed Jul. 13, 2001, Danish Application No. PA 2001 01559 filed Oct. 24, 2001 and PCT/DK02/00487 filed Jul. 11, 2002.

The present invention concerns a method for in situ measuring of evaporation from a surface and an apparatus for measuring the evaporation from a surface. Curing technology concerns, among other things, adjustment and control of temperature and humidity conditions in hardening constructions and elements of concrete. The curing technology comprises further e.g. measurement/adjustment/control of moisture conditions in the early hardening phase of the concrete in order to achieve an optimal development of properties in the hardening concrete ("moisture curing").

During the latest decades, the development within concrete technology has formed the basis of a new concept: High-Performance Concrete. Typically, a water/cement ratio (w/c ratio) in the range of 0.40–0.60 is used for conventional concrete, but today's superplasticizers have made it possible to manufacture relatively fluid concrete with a w/c ratio of 0.20–0.30 when up to 20% silica fume is added. With these extremely dense concretes, concrete strengths of 200–400 MPa can be achieved industrially, whereas in comparison, conventional concrete typically has concrete strengths of 30–50 MPa.

Danish concrete research has had a central role in the theoretical and experimental development of this new concept and several Danish companies are today involved in the industrial implementation of High-Performance Concrete in targeted special productions.

In curing technology terms the concept High-Performance Concrete means that the requirements for optimal and controlled moisture curing during hardening are significantly increased. At low w/c ratios, even modest losses of water in the early hardening phase may be detrimental to the subsequent hardening and property development of concrete.

In the field of High-Performance Concrete, it can be expected that the coming years will witness a growing need for simple, operational methods for the measurement/adjustment/control of the moisture curing conditions of concrete in the manufacturing process.

PRESENTATION OF PROBLEM

During the first hours after mixing and casting, concrete is plastic and workable. The setting of the concrete—the time when it stiffens and becomes rigid—will normally occur 4–8 hours after adding water and mixing. During the setting period and immediately thereafter, the strength of the concrete is very low, and in this condition the cast concrete is very susceptible to any form of mechanical influence.

If concrete is exposed to heavy desiccation in the period before and during setting, detrimental cracking in the concrete surface may occur. These cracks—plastic shrinkage cracks—occur because the surface tension of the pore water in menisci builds up critical capillary tensile stresses in the hardening binder phase.

For conventional concrete, crack damage due to plastic shrinkage in the early hardening phase traditionally presents a problem when casting at high temperatures, low relative humidity and high wind velocity. The damage is likely to be particularly severe when concrete/mortar is cast in thin layers, e.g. when shotcreting in connection with repair work. As result of the thinner layers, even a limited loss of water by evaporation may in these cases cause crack damage due to plastic shrinkage.

According to the American Concrete Institute Report ACI 305R-91, actual crack damage can be avoided in mass concrete, i.e. concrete constructions of relatively large dimensions, if the loss of water due to evaporation in the early hardening phase is less than approx. 1 kg/m$^2$h. For thin layers of e.g. shotcrete, however, the permissible evaporation rate is much lower.

High-Performance Concrete is particularly susceptible to desiccation in the early hardening phase. This is mostly due to the coincidence of the following three aspects:

The low porosity and permeability of the concrete means that any loss due to evaporation from the surface zone can only be replaced to a limited extent by water added from the subjacent concrete.

The high concentration of solid particles in the concrete makes the system 'rigid', and as a result even a modest loss of water will 'lock' the particle system whereupon further loss of water will lead to the formation of menisci and capillary tensile stresses in the pore fluid.

The added silica fume typically has a particle dimension of 0.1 µm, which is approximately 100 times less than the average dimension of the cement particles; thus the capillary tensile stresses caused by early desiccation will accordingly be much greater than in conventional concrete.

In High-Performance Concrete, these detrimental physical phenomena are further exacerbated by the fact that a considerable degree of autogeneous shrinkage takes place in the binder phase, which adds to the tendency to crack formation during hardening.

SUMMARY OF THE INVENTION

The purpose of this invention is therefore to create a method and an apparatus for measuring the evaporation from a surface and in particular a surface consisting of a cement-stabilised material, but in general from any surface from which substances evaporate from a surface.

The following discussion of the problem will refer to the early hardening phase of a cement-based material.

The thermodynamic principles applying to the surface of wet cement-stabilised material can be compared with several other situations, such as the skin surface on an athlete or an animal, the surface of a leaf on a plant where there is a natural ongoing evaporation, or the surface of a surface-treated item such as a painted surface, where solvents from the surface treatment will evaporate in connection with the curing of the surface treatment agent. To sum up, the principle of the invention is therefore equally applicable to any type of surface which allows thermal contact between the apparatus and the surface.

MEASUREMENT OF EVAPORATION LOSS

The evaporation rate from a wet concrete surface is governed by a complex interaction between heat content and heat development in the subjacent concrete, the temperature and humidity of the ambient air and the wind velocity of the ambient. After casting, the surface temperature of the concrete will adjust in pseudo-psychrometric temperature equilibrium in relation to the ambient air. The evaporation rate from the wet concrete surface will then be influenced by a number of time-varying parameters such as:
- Air temperature $\theta_a(t)$
- Relative humidity: RH(t)
- Wind velocity at the concrete surface: v(t)
- Development of heat in the hardening concrete: Q(t)

The governing potential difference of the evaporation process is the pressure difference $\Delta p(t)$ between the partial vapour pressure in the ambient air and the partial pressure of saturated vapour at the wet concrete surface. The surface temperature of the concrete—and thus the governing potential difference $\Delta p(t)$—is significantly influenced by the convectively determined heat and moisture transfer in the boundary layer at the concrete surface, which again depends on the wind velocity in the ambient air.

This interaction between a local microclimate, environmental actions and heat development in a subjacent concrete mass complicates technical calculations and measurements.

On certain simplified conditions, approximate thermodynamic calculation formulas can be set up for this coupled moisture-heat transport in the boundary layer between the wet concrete surface and the ambient air, thereby allowing an estimation of the evaporation rate. This is illustrated in FIG. 1, which shows an example of a nomogram currently used to estimate the evaporation rate from a wet, hardening concrete surface (ACI 305R-91).

If this method for measuring/adjusting/controlling the evaporation loss from cast, hardening concrete is applied to building technology, however, it is limited by a number of factors of a practical nature.
- The parameters used for estimation of the evaporation rate vary in time and place for a given cast concrete structure.
- The estimation of a local evaporation rate requires measurement of at least 4 quantities, two of which—local wind velocity, v and local relative humidity RH—should be denoted 'transient' numerical quantities from a measuring technology point of view.
- It is difficult to register the influence of the heat of hydration on the surface temperature of the concrete at the critical time of setting with standard measuring equipment.
- The necessary measuring equipment and the necessary experience to estimate the evaporation rate from a wet surface require an extensive knowledge of measuring techniques.

The overall idea of the apparatus according to the invention is to measure the actual, integrated evaporation loss from a wet hardening concrete surface instead of making an approximate estimation of instantaneous values of the evaporation rate from the concrete on the basis of time-varying parameters that are difficult to measure. This measuring concept has been tested with different prototypes of the apparatus according to the invention.

The above-mentioned problems and the overall idea behind the invention led to the design of an apparatus according to the invention for in situ measuring of evaporation of substances from a surface, in which the apparatus is distinct in that the apparatus comprises an evaporation surface with a well-defined area consisting of a hydrophilic, porous material and the fact that the evaporation surface is in open connection with a reservoir containing the same substance which evaporates from the surface.

When, during use, the apparatus is brought into intimate contact with a surface, the provided apparatus with its hydrophilic, porous surface which acts as an evaporation surface, will ensure that identical boundary conditions will exist immediately above the evaporation surface and immediately above the material surface.

In case of cement-based materials, and in particular concrete as described above, the substance evaporating from the surface will primarily be water. By providing a reservoir with water, the conditions of evaporation above the concrete surface will be completely identical to the conditions of evaporation above the evaporation surface of the apparatus. The porous, hydrophilic material which is in direct open connection with the reservoir will therefore suck fluid out of the reservoir as a result of the evaporation. This makes it possible to record the actual, integrated evaporation of a substance from the surface.

In one embodiment of the invention, the reservoir is a capillary tube. A capillary tube is characterised in that it has a very narrow internal diameter and therefore even minor evaporation from the evaporation surface will result in a measurable displacement of the surface of the substance (the liquid surface) in the capillary tube.

In a further preferred embodiment of the invention, the extent of evaporation from the surface can be read off a scale mounted on the apparatus. By testing the apparatus under controlled conditions, a scale can be calibrated to suit the exact surface on which the apparatus is intended to be used. In the following a large number of tests are described during which the actual evaporation loss was recorded under controlled conditions by means of a scale, whereupon a corresponding calibrated scale was provided for use of the apparatus in the determination of evaporation loss from hardening cement surfaces.

In a similar way as described below for concrete surfaces, it is possible to test surface-treated surfaces, the skin surface of an athlete or an animal or to register the evaporation from plant leaves. It is therefore possible to provide calibrated scales to measure the evaporation from different surfaces.

In a further preferred embodiment of the invention, the substance in the capillary tube is coloured and the tube sealed at one end so that the seal must be broken before use or alternatively the capillary tube is open at the end which is not connected to the evaporation surface. When using the latter version of the apparatus, the tube is filled with liquid in situ. One way of doing this is to dip the open end into the liquid which will then fill the capillary tube as a result of capillary suction.

The latter embodiment is preferred as air bubbles may occur in the capillary tube of the first mentioned version during transportation or prolonged storage despite the packaging being almost completely tight. This problem is completely avoided if the capillary tube is filled in situ immediately or a short time before the measurements are taken. In addition, the integrated evaporation loss from the surface is easy to read in that the substance in the capillary tube is coloured and therefore stands out.

For the apparatus to be able to simulate the actual evaporation process it is a condition that the apparatus is in good thermal contact with the surface from which evaporation takes place. In a further preferred embodiment of the invention, the evaporation surface and capillary tube have therefore been provided on a heat-conducting base plate. By ensuring this thermal contact between the apparatus and the surface where evaporation is to be measured it is ensured that the liquid above the evaporation surface is exposed to the same boundary conditions including the hydration heat from the surface.

One particular embodiment of the invention features a base plate made of aluminium or synthetic material with an aluminium coating on the side which is intended for the intimate thermal contact with the surface. This embodiment is especially preferred because aluminium is a metal which is particularly heat-conductive.

In a further preferred embodiment, the porous, hydrophilic material has been selected from e.g. gypsum, felt, fibrous materials or sintered ceramic materials. In the following some specific embodiments are described where the evaporation surface is made of hardened gypsum. The nature of the porous, hydrophilic material depends on the use for which the apparatus is intended. The most important aspect in this context is to use a porous, hydrophilic material which is able to transport the substance from the capillary tube to evaporation from the evaporation surface in circumstances that are identical to those of the surface where evaporation loss is to be recorded.

In a further preferred embodiment, the scale is provided on the capillary tube or the base plate calibrated to show the measured, integrated evaporation loss of the substance in the capillary tube from the evaporation surface of the apparatus and expressed as a well-defined unit such as e.g. $kg/m^2$. It thus becomes a simple and easy task for the user to continuously and unambiguously register the evaporation loss from the surface.

In a further preferred embodiment of the invention means are provided for electronic data collection on the apparatus. The means can comprise an ICC chip (Integrated Circuit Card) with interface. The evaporation can be registered on the basis of e.g. resistance measurements in the capillary tube where the resistance increases proportionally to the evaporation from the surface or by directing a laser beam from e.g. a laser diode towards the surface of the liquid in the capillary tube and with a light-sensitive diode record interference at reflection from the surface, or alternatively a number of light-sensitive diodes can be positioned alongside the capillary tube corresponding to a measuring scale whereby changes in the angle of light on the diode indicate the passage of the surface of the liquid in the capillary tube and thereby the evaporation from the evaporation surface. The chip can be programmed to log data at certain defined intervals which will permit direct download of data via interface for further processing on computer.

In a further preferred embodiment, the apparatus is made of flexible and heat-conducting material whereby the apparatus can be adapted for use on other types of surfaces. In this connection in particular skin surfaces. In this application, the apparatus is designed as a band aid-like product which can adhere to the skin.

In certain embodiments of the invention, the apparatus could be manufactured as a disposable meter. In other embodiments of the apparatus according to the invention, and especially where electronic equipment is used and the meter therefore is more expensive, the apparatus is designed in such a way that the reservoir/capillary tube can be replaced and the evaporation surface be cleaned or replaced.

BRIEF DESCRIPTION OF THE DRAWINGS

In the following, the invention will be explained with reference to the attached drawing, in which.

DETAILED DESCRIPTION OF THE PREFERRED EMBODIMENTS

Figure 2A:
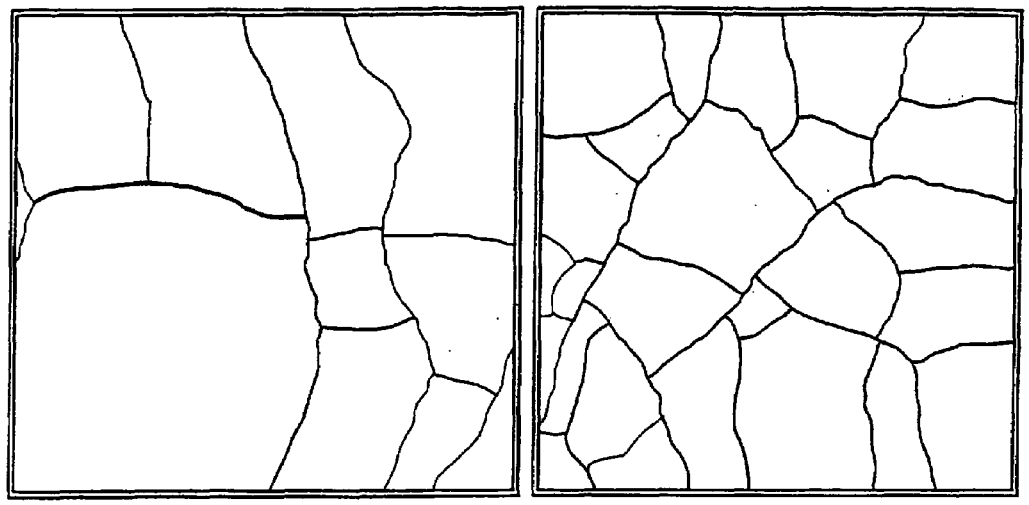
FIGS. 2a and 2b show the effect of wind and desiccation respectively in the early hardening phase.

FIG. 2a shows the effect of wind influence in the early hardening phase. Both specimens have binder phase of high-performance-concrete with a w/c ratio of 3.30, added 20% silica fume. The specimen to the left has been drawn on the basis of a photograph showing the condition after 16 hours of hardening in static air at 20° C. and a relative humidity of 50%. The specimen to the right in the same air climate has been exposed to wind velocities of 4–5 m/s. The specimens shown are 15×15 cm and the thickness of the items is 10 cm. It is evident that the wind load has worsened the crack damage as a result of plastic shrinkage.

Figure 2B:
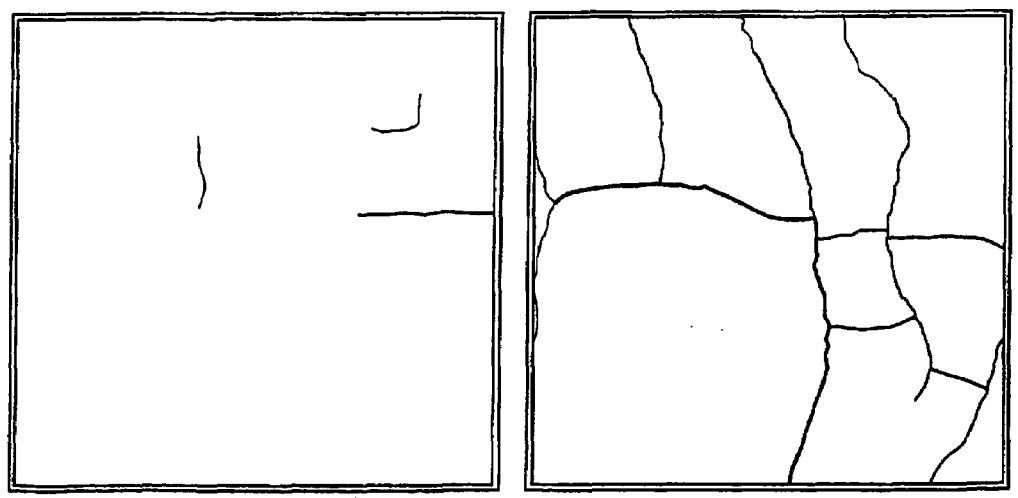

FIG. 2b shows the effect of desiccation in the early hardening stage. The specimen to the left shows a binder phase of conventional concrete with w/c ratios of 0.5 and with 0% added silica fume. The specimen to the right shows a binder phase of High-Performance-Concrete with w/c ratios of 0.3, added 20% silica fume. Both specimens have been drawn on the basis of a photograph showing the condition after 16 hours of hardening in static air at 20° C. and a relative humidity of 50%. The specimens shown are 15×15 cm and the thickness of the items is 10 mm. The binder phase of conventional concrete to the left shows early signs of cracking; the binder phase of High-Performance Concrete to the right shows serious cracking due to plastic shrinkage.

Figure 3A:
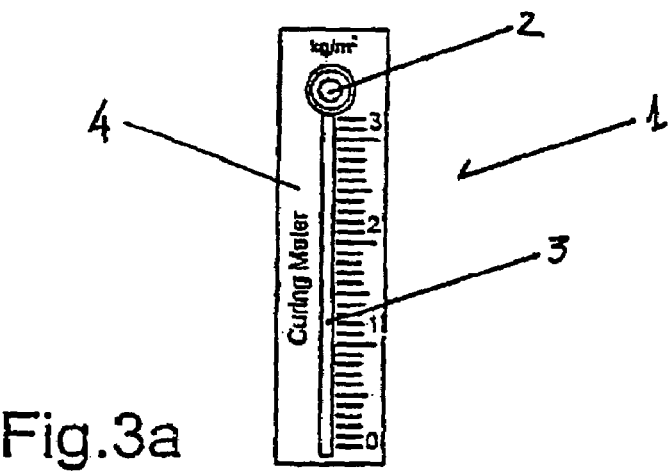
FIG. 3a shows an apparatus according to the invention.

Examples of manufactured and tested prototypes of the apparatus (1) according to the invention are shown in FIG. 3a. The measuring system consists of a circular evaporation surface (2) of gypsum with a water/gypsum ratio of 0.60. An embedded capillary tube (3) with inner aperture of Ø 0.9 mm is in hydraulic contact with the evaporation surface (2).

The evaporation surface with capillary tubes is either mounted on top of a 0.5×15×65 mm aluminium base plate (4) or embedded in a 1.5 mm acrylic plate onto which an aluminium plate of similar dimensions has been glued.

The capillary tube (3) contains water to which colour is added. During measuring, the apparatus is brought into close thermal contact with the wet sublayer so that evaporation surface and sublayer have the same temperature The scale on the base plate (4) has been calibrated so that the evaporation loss from the gypsum surface can be read directly in units of $kg/m^2$.

In case of industrial mass-production of the apparatus, the following two embodiments would be possible:
1. The apparatus is injection moulded in a hard type of plastic with low water absorption, e.g. Polystyrene. The capillary tube can be either a separate glass tube mounted in a guide groove or it can be a cast opening in the base plate itself. The evaporation surface is formed in a circular gypsum-filled cavity at the end of the capillary tube. The total thickness of the base plate will be 1.6–1.8 mm. The final appearance of the apparatus will be approximately as the prototype shown in FIG. 3 or
2. the base plate (4) is moulded and punched in one operation from a 0.2–0.3 mm aluminium plate; during moulding, an approximately 1.4 mm deep groove for the capillary tube is formed together with a well-defined circular cavity of the same depth for the gypsum-filled evaporation surface. The thermal properties of this embodiment will be superior to the embodiment described under 1) due to the high thermal diffusivity of aluminium.

The sensitivity and measuring range of the apparatus can be adapted to a large number of different applications through the choice of diameter ratio between the capillary tube and the evaporation surface.

Figure 3B:
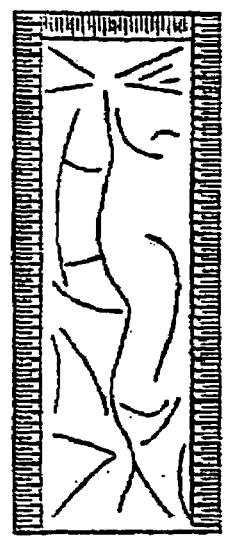
FIG. 3b shows an apparatus according to the invention in sealed packaging.

For application in practice, the end of the capillary tube (3) may protrude from the base plate (4) and be sealed. After vacuum filling of the capillary tube and the evaporation surface (2), the base plate is enclosed in a water-saturated, algae-proof fibrous folder with diffusion-proof seal as shown in FIG. 3b.

For measuring purposes, the seal is broken, the end of the capillary tube is broken off and the apparatus is pressed into the concrete surface on the chosen measuring point.

As described above, another embodiment can feature an empty capillary tube that is open at the end that faces away from the evaporation surface. The capillary tube is filled immediately before use by immersing it in the liquid.

A number of measurements have been made with the manufactured prototypes in order to document the operation of the apparatus. During these measurements, the apparatus was mounted on specimens with well-defined evaporation areas placed on a digital scale with 0.001 g solution, see FIG. 6. The actual evaporation loss in kg/m² from specimens could thus be registered and compared with the results shown by the apparatus. The wind velocity v (m/s) and RH (%) above the surface of the specimen were varied during the tests.

During the measuring process, the temperature $\theta_a$ and relative humidity RH of the ambient air as well as the wind velocity v and the temperature of the wet surface $\theta_t$ were recorded.

FIG. 4a–d show an example of such measuring process where a specimen has been exposed to a complex desiccation action.

Figure 4A:
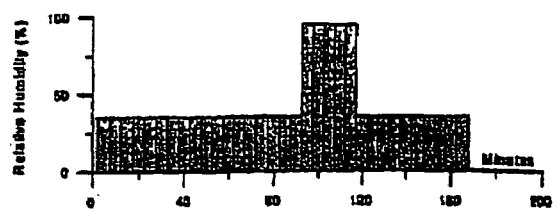
FIG. 4a–d show examples of a measuring programme when testing the apparatus according to the invention.

FIG. 4a shows the relative humidity RH above a free specimen in the early hardening phase. RH was approx. 35% apart from a period with cover during which RH was 90–100%.

Figure 4B:
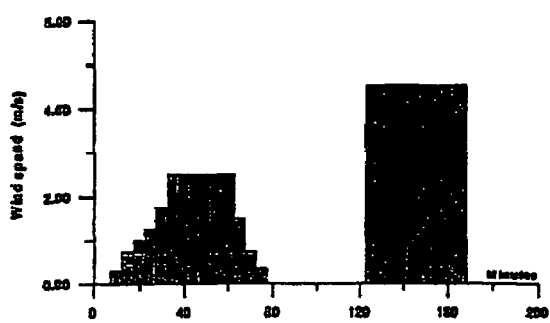

FIG. 4b shows the approximate wind velocity at the surface of the specimen in the early hardening phase. As shown on the figure, the wind velocity was kept constant for part of the time and then increased or decreased, respectively, during measuring. Maximum wind velocity 4–5 m/s; the specimen was surrounded by static air during certain periods.

Figure 4C:
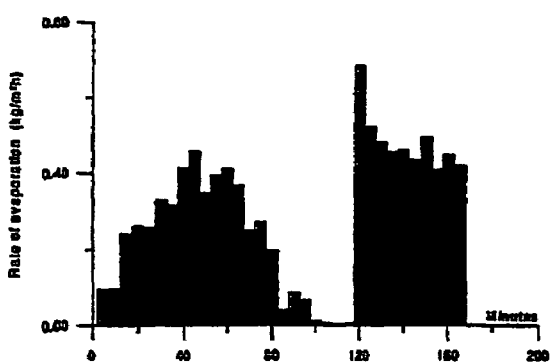

FIG. 4c shows the measured evaporation rate from the specimen during measuring. It should be noted that the evaporation rate has varied from approx. 0 kg/m²h during the period with cover to approx. 0.70 kg/m²h during the period with maximum wind velocity. Note especially that the maximum evaporation rate occurs immediately after the cover period at which time the temperature of the specimen has risen to a value close to the humidity in the room. As the psychrometric cooling reduces the temperature of the specimen, the evaporation rate again decreases.

Figure 4D:
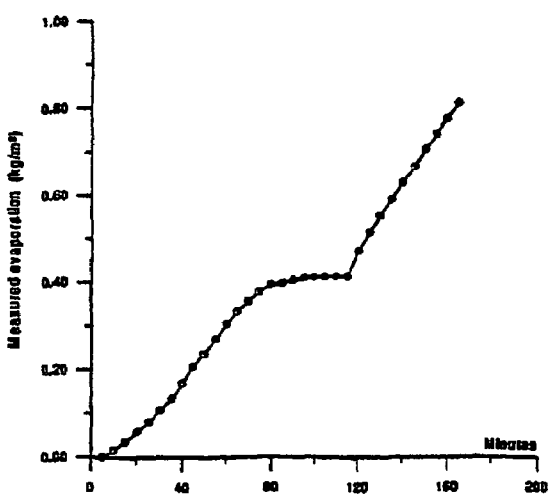

FIG. 4d shows the measured, total evaporation loss from the specimen during measuring. The curve represents the time integral of the evaporation rate shown in FIG. 4c. During testing, initial crack indication could be seen on the surface after 100–120 minutes of exposure, and after 140–150 minutes, there were distinct, deep, open cracks in the surface. This supports the theory that the risk of formation of plastic shrinkage cracks is highly dependent on the thickness of the specimen.

FIG. 4a shows changes in the relative humidity RH and FIG. 4b shows changes made in the wind velocity v during the test. As shown in FIG. 4c, the evaporation rate is significantly influenced by these changes in boundary conditions. The total measured evaporation loss from the specimen during testing is indicated on FIG. 4d.

Figure 1:
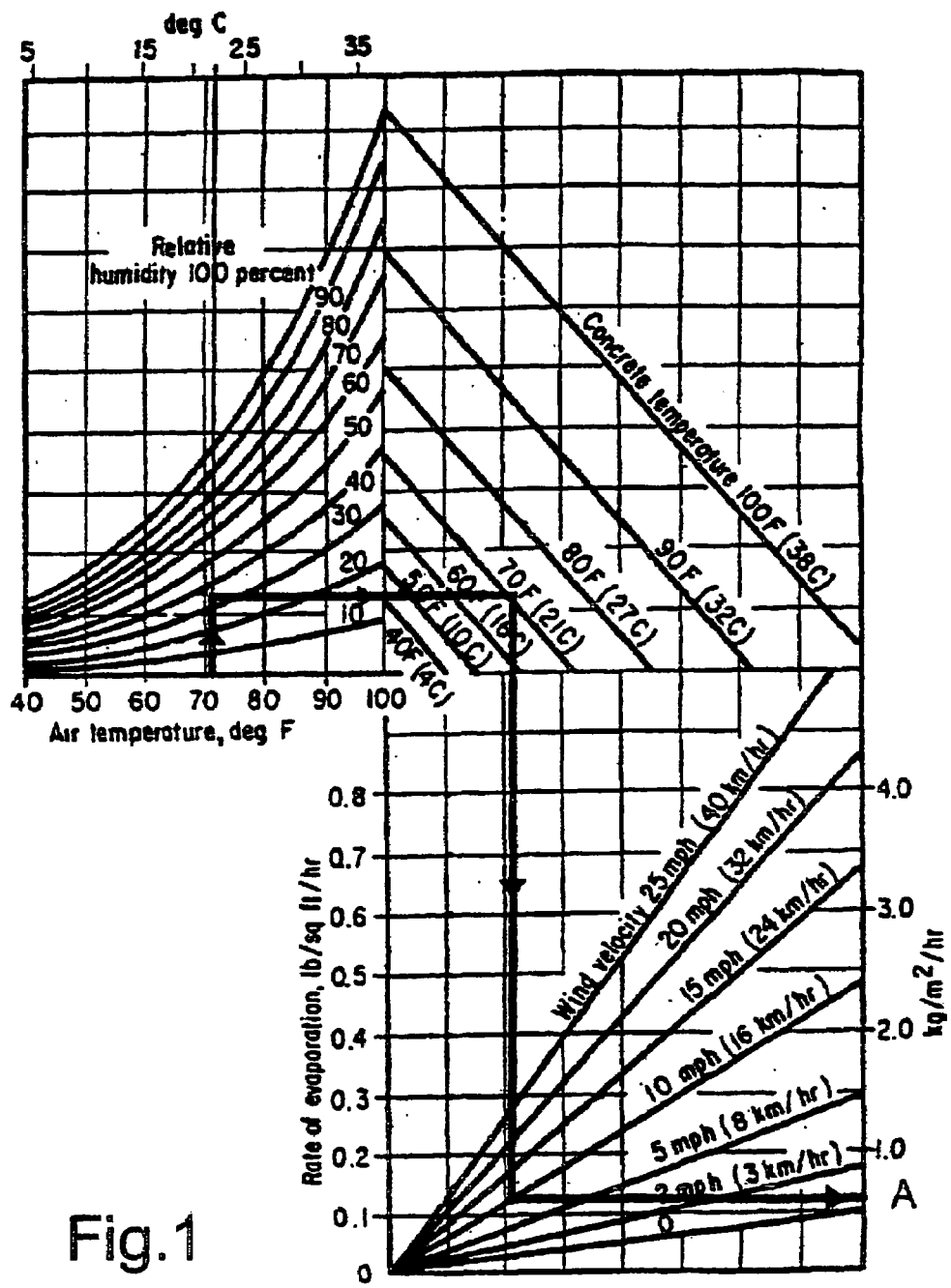
FIG. 1 illustrates a standard nomogram routinely used for estimating the evaporation rate from a wet hardening concrete surface according to ACI 305R-91 (Hot Weather Concreting).

As an example, a evaporation rate of 0.70 kg/m²h was measured after 120 minutes and immediately following the period with cover. At this point in time, the temperature of the specimen matches the temperature of the ambient air, i.e. approx. 22° C., the relative humidity is approx. 35%, and the wind velocity approx. 4.5 m/s (approx. 16 km/h). Using these boundary conditions it is possible, as indicated at (A) in the ACI 305R-91 nomogram (FIG. 1), to estimate by calculation an evaporation rate of approx. 0.7 kg/m²h, which is in close accordance with the measured value. As seen from FIG. 4c, an ongoing evaluation of the desiccation action by means of nomograms is not an expedient measurement technique, as four time-dependent parameters are included in each determination of the evaporation rate. Furthermore, in practice the governing curing parameter is the integrated evaporation loss corresponding to FIG. 4d.

In contradistinction, the tests that have been carried out with the apparatus show that despite these complex changes in boundary conditions, the integrated evaporation loss can be easily and very accurately determined using the technique according to the invention. In the desiccation test that was performed, the evaporation loss measured by the apparatus was compared with the evaporation loss shown in FIG. 5.

Figure 5:
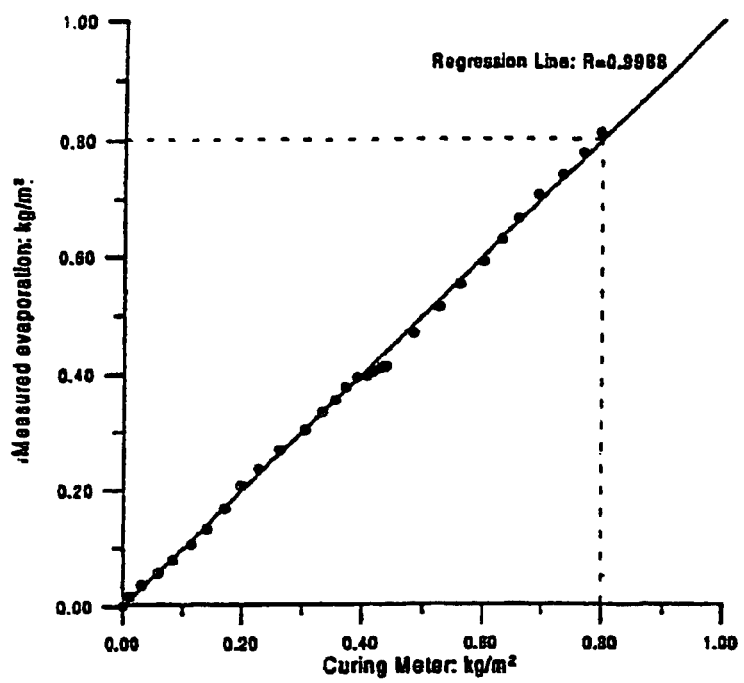
FIG. 5 shows results measured with the apparatus compared with actually measured weight loss.

FIG. 5 is an example of a test of the apparatus under the boundary conditions for hardening indicated in FIG. 4. The specimen examined is binder phase with w/c ratios of 0.30, added 20% silica fume. The figure shows the measured evaporation loss in kg/m² compared with the values read off a calibrated apparatus. The apparatus used was a prototype with rectangular evaporation surface; a design with a number of production-related benefits. The test set-up is shown in FIG. 6.

Figure 6:
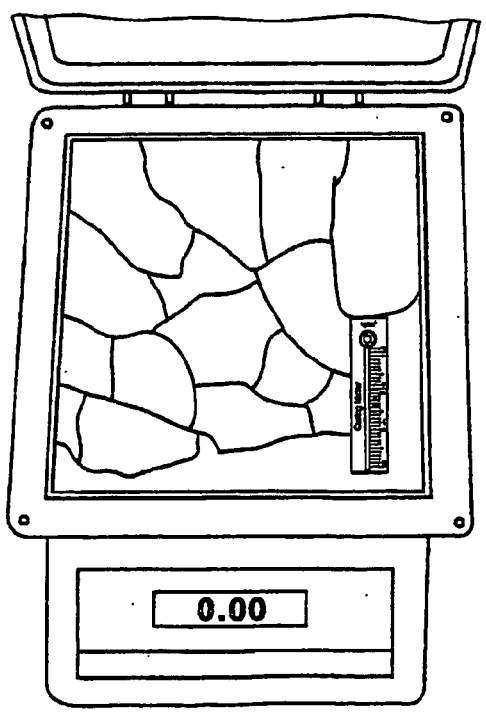
FIG. 6 shows a test set-up for testing the apparatus.

FIG. 6 shows a test set-up used for testing the prototype of the apparatus. The examined binder phases are cast in a 15×15 cm mould. After casting, the apparatus is mounted in the binder phase and the mould is placed on the scale with 0.001 g solution, as shown.

Technically, the apparatus is therefore characterised in that:

An evaporation surface with a well-defined area, made from a hydrophilic, porous material, is ensured thermal contact with the surface of newly cast concrete so that the local microclimate above the evaporation surface given by the following time-varying evaporation parameters Surface temperature $\theta(t)$, air temperature $\theta_a(t)$, relative humidity RH(t) and wind velocity v(t) is identical to the corresponding local microclimate above the surrounding concrete surface.

The pseudo-psychrometric temperature drop of $\theta(t)-\theta'(t)$ in relation to the ambient air temperature $\theta_a(t)$ is the same for the evaporation surface of the meter as for the surface of the surrounding concrete.

Water is added to the evaporation surface from a reservoir such as an embedded capillary tube designed in such a way that the amount of water w (kg/m²) evaporated from the evaporation surface can be read on a calibrated scale at the capillary tube.

The total evaporation loss, w (kg/m²), from the evaporation surface registered at any point in time, equals the measured integrated effect of the time-varying mutually independent evaporation parameter on the concrete surface: Surface temperature $\theta(t)$, air temperature $\theta_a(t)$, relative humidity RH(t) and wind velocity v(t).

The method used by the apparatus is characterised in that:

It is an inexpensive, mass-producible dispensable meter which after simple stripping can be activated and brought to function by indentation in a newly cast concrete surface.

The measurement of the integrated evaporation loss from a wet, hardening concrete surface can be carried out fast and easily on building sites by personnel without specific technical knowledge about methods for measuring temperature and humidity.

The measurement makes it possible to prescribe well-defined and controllable requirements to moisture curing in work specifications for the concrete work.

In a simple and inexpensive manner it is possible for the person carrying out the work by measurement to document compliance with requirements in work descriptions for the finishing moisture treatment of the concrete.

The measurement replaces an existing complicated and expensive technical evaluation of the evaporation loss from a wet, hardening concrete surface and it is at the same time assumed to render a higher degree of certainty and accuracy in the determination of this evaporation loss.

The apparatus thus creates a new method for in situ measuring of water evaporation from concrete surfaces in the early hardening phase. When determining the extent of desiccation in the early hardening phase, and in contradistinction to the methods used up until today, the apparatus provides a method for simple, certain and more accurate determination of evaporation loss from hardening concrete; this, in turn, makes it possible to prevent curing problems including detrimental crack damage due to plastic shrinkage.

One specific embodiment of the invention targets the following groups:

Target group A: Companies involved in the casting of concrete structures, concrete pavements, concrete pipes, concrete articles or repair of concrete with conventional concrete. In these cases, the apparatus can be applied for in situ measurements/adjustment/control of the desiccation action to which concrete is exposed in the early hardening phase. For these kinds of concrete work the code of practice today stipulates a number of specific requirements to moisture curing that are difficult to document. An example of such requirements is illustrated on page 17 and 18, which are an extract from DS (Danish code) 482:199. In connection with so-called Hot Weather Concreting, there is a particular need for methods for measuring/adjustment/control of desiccation action on building sites.

Target group B: Companies involved in industrial implementation and utilisation of High-Performance Concrete. The binder phase in modern High-Performance Concretes is particularly susceptible to desiccation action. In curing technology this means that the requirements for optimal and controlled moisture curing are significantly increased for manufacture of these kinds of products. The apparatus makes it easy to comply with these stricter requirements to moisture curing. The market for specialised products made from High-Performance Concrete has been on the increase in recent years.

Extract from DS 482:1999 Regarding Desiccation

DS 482:1999

9.7 Protection of the Concrete in the Hardening Period

The concrete should be protected against harmful effects in the hardening period.

NOTE: Harmful effects may e.g. be direct sunlight, strong wind, frost, water and wash-out. The effects may occur during handling, positioning, compression or at any time before the end of the hardening period.

Free surfaces should be protected against critical desiccation and the construction as a whole should be protected against harmful temperature influences.

Protection against desiccation in a passive environmental class should only be carried out if specifically requested.

NOTE: Desiccation protection should normally be requested for interior surfaces and floors.

9.7.1 Desiccation

The concrete should be protected against critical desiccation during the hardening period in order to avoid crack formation due to plastic shrinkage and in order to ensure that sufficient water is present for the hydration of the cement.

NOTE: The above makes heavy demands on the latest possible establishment of protection and the duration of protection. Plastic shrinkage cracks may occur up until the time of setting. The setting time of the concrete is determined with reference to DS423.17 or on the basis of the heat development of the concrete with reference to DS 423.37.

9.7.1.1 Timing of Establishment of Protection

All free surfaces should be protected against critical desiccation as indicated in table 9.7.1.1a as soon as possible after the casting of the concrete.

TABLE 9.7.1.1a

Maximum permissible water evaporation before desiccation protection is established.

| The contents of the concrete, X of FA + MS in % weight of C + FA + MS | The contents of the concrete, Y of MS in % weight of C + FA + MS | Maximum amount of water evaporated from the surface |
| --- | --- | --- |
| X > 15% | Y > 5% | 1.5 kg/m² |
| 15% ≧ X > 5% | 5% ≧ Y > 0% | 3.0 kg/m² |
| 5% ≧ X | Y = 0% | 6.0 kg/m² |

The amounts of water indicated in table 9.7.1.1a correspond to layers with a thickness of 0.2 m or more. For thicknesses of less than 0.2 m, the amount of water should be reduced proportionally. Protection against desiccation should, however, be in place at the latest by the time the setting begins.

NOTE: If no documentation is provided to prove that the requirements laid down in table 9.7.1.1a have been complied with, protection of the surface should be established before expiry of the periods allowed from time of casting as per table 9.7.1.1.b.

TABLE 9.7.1.1b

Deadline for establishment of protection against desiccation at wind velocities of max 5 m/sec.

| The contents of the concrete, X of FA + MS in % weight of C + FA + MS | The contents of the concrete, Y of MS in % weight of C + FA + MS | Outdoor works | Indoor works Temperature of concrete | | |
|---|---|---|---|---|---|
| | | | >30° C. | 15–30° C. | <15° C. |
| X > 15% | Y > 5% | 1 hour | 1 hour | 1.5 hours | 2 hours |
| 15% ≧ X > 5% | 5% ≧ Y > 0% | 2 hours | 2 hours | 3 hours | 4 hours |
| 5% ≧ X | Y = 0% | 4 hours | 4 hours | 6 hours | 8 hours |

The times indicated in table 9.7.1.2a correspond to layers with a thickness of 0.2 m or more. For thicknesses of less than 0.2 m, the times should be reduced proportionately.

9.7.1.2 Duration of Protection

In order to ensure sufficient hydration and density of the concrete surface, the surface of the concrete should be protected against critical desiccation as indicated in table 9.7.1.2a.

TABLE 9.7.1.2a

Minimum duration of desiccation protection expressed as relative hydration (expressed on the basis of the adiabatic heat development of the concrete).

| Environmental class | P | M | A | E |
|---|---|---|---|---|
| Relative hydration % | 40 | 60 | 85 | 90 |

NOTE: The duration is calculated on the basis of the measured, adiabatic heat development parameters of the concrete. If the heat parameters have not been defined, the values indicated in table 9.7.1.2b are normally sufficient to avoid critical desiccation.

TABLE 9.7.1.2b

Minimum duration of desiccation protection. Age[1] of concrete measured as number of hours of maturity[2] at the earliest time of removal of the protection.

| Environmental class: | P | M | A | E |
|---|---|---|---|---|
| w/c > 0.55 | 15 | — | — | — |
| 0.55 ≧ w/c > 0.45 | 15 | 36 | — | — |
| 0.45 ≧ w/c > 0.40 | 12 | 24 | 120 | — |
| 0.40 ≧ w/c | 12 | 24 | 96 | 120 |

[1]If the setting of the concrete begins more than 5 hours after mixing, the indicated maturing times will change accordingly.
[2]The maturity of the concrete is documented by measuring the surface of the concrete at a depth of max. 10 mm.

The required desiccation protection can be provided by:
leaving the mould and covering the free surfaces of the concrete
covering with vapour-proof membranes
maintaining a sufficiently high relative humidity in the surroundings
keeping the surfaces wet at all times; repeated wetting and drying of the surfaces should nevertheless be prevented
using sealant provided the sealing agent has an efficacy factor of at least 75% determined by reference to test method TI-B33 unless otherwise requested in the project specification.
wetting should only begin once the fresh concrete surface can tolerate this.

The invention claimed is:

1. Apparatus for in situ measuring of evaporation of a substance from a surface, wherein the apparatus has an evaporation surface of a well-defined area and consisting of a hydrophilic, porous material; and in that the evaporation surface is in open connection with a reservoir containing the same substance as the one evaporating from the surface, wherein the reservoir is a capillary tube and in that the apparatus is provided with a calibrated scale on which the amount of evaporation from the surface can be directly read.

2. Apparatus according to claim 1, wherein color is added to the substance in the tube and in that the capillary tube is either sealed at one end, in which case the seal is broken before use, or open at the end which faces away from the evaporation surface, in which case the capillary tube is filled before use.

3. Apparatus according to claim 1, wherein the evaporation surface and the capillary tube are provided on a heat-conducting base plate.

4. Apparatus according to claim 3, wherein the base plate is an aluminum plate or a synthetic plate with aluminium coating on the side intended for intimate, thermal contact with the surface.

5. Apparatus according to claim 1, wherein the porous, hydrophilic material has been selected from one of the following groups: gypsum, felt, fibre materials and/or sintered ceramic materials.

6. Apparatus according to claim 1, wherein the scale on the apparatus has been calibrated to show an integrated evaporation loss of the substance from the evaporation surface of the apparatus.

7. Apparatus according to claim 1, wherein the capillary tube is integrated into the base plate.

8. Apparatus according to claim 3, wherein the base plate is made of a flexible, heat-conducting material.

9. Apparatus according to claim 1, wherein the apparatus is provided with means for electronic data collection including in particular the time-varying and/or integrated evaporation loss and means for electronic communication with external units.

10. Method for in situ measuring of evaporation of a substance from a surface according to which the evaporation is measured with an apparatus according to claim 1, in which
the sealed end of the capillary tube is broken or alternatively the capillary tube is filled prior to use;
the evaporation surface is brought into intimate thermal contact with the surface, so that the evaporation conditions for the surface and the evaporation conditions for the evaporation surface on the apparatus are the same, which makes it possible to read the total evaporation from the surface on the capillary tube.

11. Method according to claim 10, wherein the surface is of a cement-based material and the capillary tube is calibrated to register the evaporation loss from a cement-based surface whereby the correlated, integrated evaporation loss from the surface of the cement-based material is registered.

* * * * *